United States Patent [19]

Illy et al.

[11] Patent Number: 5,072,055

[45] Date of Patent: Dec. 10, 1991

[54] PROCESS FOR THE PREPARATION OF SUBSTITUTED PHENOLS

[75] Inventors: Hugo Illy, Reinach; Ronald Salathé, Magden; Rudolf Schwabe, Nuglar, all of Switzerland

[73] Assignee: Ciba-Geigy Corporation, Ardsley, N.Y.

[21] Appl. No.: 594,876

[22] Filed: Oct. 9, 1990

[30] Foreign Application Priority Data

Oct. 12, 1989 [CH] Switzerland .................. 3721/89

[51] Int. Cl.$^5$ .............................................. C07C 37/50
[52] U.S. Cl. .................................................. 568/805
[58] Field of Search .................................. 568/805, 806

[56] References Cited

U.S. PATENT DOCUMENTS

| | | | |
|---|---|---|---|
| 2,295,673 | 9/1942 | Meharg et al. | 568/805 |
| 2,295,674 | 9/1942 | Meharg et al. | 568/805 |
| 3,658,920 | 4/1972 | Lawley et al. | 568/805 |
| 4,085,132 | 4/1978 | Park et al. | 560/75 |
| 4,228,297 | 10/1980 | Haeberli et al. | 560/75 |
| 4,230,896 | 10/1980 | Daly | 568/805 |
| 4,533,767 | 8/1985 | Talley | 568/805 |

OTHER PUBLICATIONS

G. H. Stillson et al., J. Am. Chem. Soc. 67, 304 (1945).

*Primary Examiner*—Werren B. Lone
*Attorney, Agent, or Firm*—Luther A. R. Hall

[57] ABSTRACT

The substituent X in the phenols of the formula:

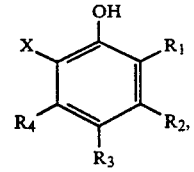

wherein $R_1$ to $R_4$ are hydrogen or unsubstituted or substituted alkyl, alkenyl or alkynyl, and X is secondary or tertiary alkyl of 3 to 9 carbon atoms, can be removed by heating said phenols in the presence of an alkali metal hydrogensulfate.

6 Claims, No Drawings

PROCESS FOR THE PREPARATION OF SUBSTITUTED PHENOLS

The present invention relates to a novel process for the preparation of substituted phenols.

Phenols which are substituted in specific positions are often used as starting materials or intermediates for the synthesis of final products having a wide range of properties. For example, substituted phenols having a free ortho-position are much in demand as starting materials for the preparation of UV absorbers of the benzotriazole type, as described, for example, in European patent application 0 157 160.

Such phenols are usually prepared by dealkylation of ortho-substituted phenols which are ordinarily obtainable from the coal-tar industry, or they are obtained, for example, by Michael addition of olefinic compounds to appropriate phenols. Reference is made in this connection to U.S. Pat. Nos. 4,085,132 and 4,228,297.

The dealkylation, specifically debutylation, of substituted phenols has been described by D. R. Stevens in Ind.Eng.Chem. 35, No. 6, 655 (1943) and by G. H. Stillson et al. in JACS 67, 305 (1945) using o-butylated cresols. They found that these debutylation reactions are catalysed by sulfuric acid, sulfuric acid esters and aromatic sulfonic acids. The removal of methyl groups from the investigated o-butylated cresols, however, has not been observed. A similar result also is described in British patent 1 183 984, where the debutylation of phenols substituted in ortho-position by tert-butyl is carried out using $Fe_2(SO_4)_3 \cdot xH_2O$.

The drawback of these processes is, however, that they do not proceed selectively enough with respect to the often-desired dealkylation of only one single ortho-position. The consequence is that the resultant products are consistently mixtures of compounds which are dealkylated in one ortho-position and in both ortho-positions. This inhomogeneity of the products often prevents their direct further processing and requires troublesome separation operations to isolate the desired product which is dealkylated in one ortho-position.

Hence it is the object of this invention to provide a process for the preparation of substituted phenols in which the dealkylation proceeds more selectively than the aforementioned processes and by means of which phenols which are dealkylated in only one ortho-position are obtained in high yield.

This object is attained in the practice of this invention by using an alkali metal hydrogensulfate as catalyst for dealkylating substituted phenols.

Accordingly, the present invention relates to a process for the preparation of phenols of formula

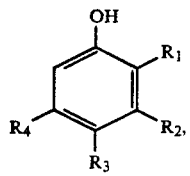
(1)

wherein $R_1$, $R_2$, $R_3$ and $R_4$ are each independently of one another hydrogen, unsubstituted or substituted alkyl of 1 to 12 carbon atoms or unsubstituted or substituted alkenyl or alkynyl of 2 to 12 carbon atoms, by heating phenols of formula

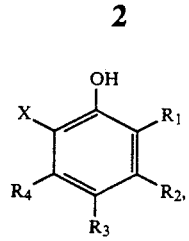
(2)

wherein X is a secondary or tertiary alkyl group of 3 to 12 carbon atoms, and $R_1$, $R_2$, $R_3$ under $R_4$ have the given meanings, in the presence of an acid catalyst, which process comprises heating said phenols of formula (2) to a temperature above their melting point to remove the substituent X, in the presence of an alkali metal hydrogensulfate as catalyst, allowing the melt to cool and, if desired, isolating the phenols of formula (1).

The invention further relates to the substituted phenols so obtained and to the use thereof for the synthesis of UV absorbers of the benzotriazole type.

In the phenols of formula (1), the substituents $R_1$, $R_2$, $R_3$ and $R_4$ are each independently of one another, unsubstituted or substituted alkyl of 1 to 12 carbon atoms or unsubstituted or substituted alkenyl or alkynyl each of 2 to 12 carbon atoms. Suitable alkyl groups are, typically, methyl, ethyl, propyl, butyl, hexyl, octyl, decyl and dodecyl as well as corresponding branched isomers. These alkyl groups may carry those substituents which do not interfere with the reaction of this invention, typically hydroxyl, alkoxy, alkoxycarbonyl, $-CO_2Z$, wherein Z is hydrogen, alkyl of 1 to 18 carbon atoms or $-(C_2H_4O)_nH$, wherein n is 1 to 12, and phenyl. Exemplary of suitable alkenyl groups are ethenyl, propenyl, butenyl, pentenyl, hexenyl, octenyl and dodecenyl, as well as the corresponding branched isomers and isomers which contain more than one double bond. Typical examples of suitable alkynyl groups are groups analogous to the aforementioned alkenyl groups, viz. ethynyl, propynyl and the like. The alkenyl and alkynyl groups may be substituted and carry the substituents mentioned in connection with the alkyl groups.

The substituent X in the phenols of formula (2) is secondary or tertiary alkyl of 3 to 12 carbon atoms and is, therefore, typically isopropyl, tert-butyl, isohexyl and isooctyl. A preferred meaning of X is tert-butyl.

In the process of this invention it is preferred to use phenols of formula

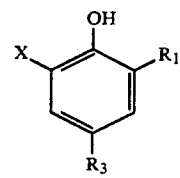
(3)

wherein $R_1$, $R_3$ and X have the given meanings.

Among these phenols, those compounds are preferred in which $R_1$ is hydrogen, alkyl of 1 to 12 carbon atoms, benzyl, phenylethyl or phenylpropyl, preferably 2-phenylpropyl, $R_3$ is alkyl of 1 to 8 carbon atoms which is unsubstituted or substituted by phenyl, $-CO_2Z$, wherein Z is hydrogen, alkyl of 1 to 18 carbon atoms or $-(C_2H_4O)_nH$, wherein n is 1 to 12, and X is tertiary alkyl of 4 to 9 carbon atoms.

Among these phenols, particularly suitable compounds are those wherein $R_3$ is methyl, tert-butyl or $-CH_2CH_2CO_2Z$, wherein Z has the given meaning.

Particularly preferred phenols are those of formula

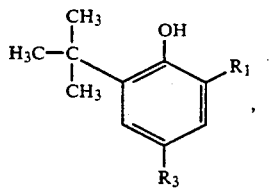  (4)

wherein $R_1$ is hydrogen or alkyl of 1 to 5 carbon atoms, preferably methyl or tert-butyl and $R_3$ is alkyl of 1 to 4 carbon atoms, preferably methyl or tert-butyl or —$CH_2CH_2CO_2CH_3$.

The substituent X can be removed from the aromatic system by heating the appropriate phenol of formula (2) to above its melting point, in the presence of an alkali metal hydrogensulfate as catalyst. The corresponding phenol of formula (1) can be isolated in a manner known per se from the resultant melt, for example by filtration of the hot melt.

It is preferred to use sodium or potassium hydrogensulfate as catalyst, conveniently in anhydrous form.

In addition to the greater selectivity of the reaction course, a further advantage of the process of this invention is that, for most purposes, the isolation of the product and the separation of the catalyst and of any by-products can be dispensed with, as the catalyst does not interfere with further reactions and by-products occur in negligibly small concentration. Further, the reaction product is almost colourless and contains no polymers formed by the removal of X.

The process of this invention is ordinarily carried out such that a phenol of formula (2) is fused in a reactor which can be evacuated. The catalyst is then added, preferably in an amount of 0.5 to 10 mol %, most preferably of 1.5 to 2 mol %, based on the phenol employed, while stirring the melt, and the temperature is then raised for 2 to 6 hours to preferably 120°-70° C. Gaseous elimination product is preferably removed by reducing the pressure in the reactor, for example to pressures in the range from 10 to 300 mbar. The melt is then allowed to cool, affording a product which can be reacted direct without further purification operations.

Suitable stirrers for stirring the melt are the known types such as anchor and gate paddle agitators, impellers and, preferably, cyclone impeller mixers.

The expulsion of gaseous elimination products from the melt with nitrogen or a boiling inert entrainer can speed up the reaction course.

It has previously been mentioned that the phenols obtainable in the process of this invention can be used for the synthesis of UV absorbers of the benzotriazole type. This procedure usually comprises coupling a diazonium salt of formula

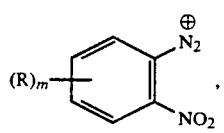

wherein R is a substituent and m is 1 to 4, with a phenol to give a o-nitroazo compound of formula

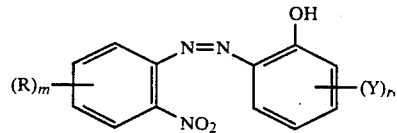

wherein Y is a substituent and r is 1 to 4 and R and m have the given meanings, and cyclising this compound to a benzotriazole of formula

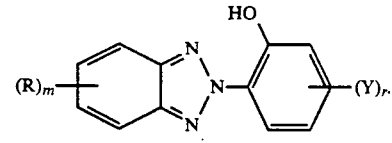

Such processes are disclosed, for example, in European patent application 0 571 60, U.S. Pat. Nos. 3,978,074 and 4,219,480, and GB patent specifications 1 494 823, 1 494 824 and 1 494 825.

The invention is illustrated by the following Examples in which percentages are by weight.

EXAMPLE 1:

In a reactor, 438 g of methyl 3-(2,6-di-tert-butyl-4-hydroxyphenyl)propionate are fused at 80° C. in a nitrogen atmosphere. Then 4.14 g of sodium hydrogensulfate are added. The pressure in the reactor is adjusted to 50 mbar. The reaction mixture is heated to 150° C. and this temperature is kept constant for 4 hours, while the presence remains at 50 mbar. After cooling the melt to room temperature, analysis of the reaction mixture gives the following composition:

| | |
|---|---|
| methyl 3-(2,6-di-tert-butyl-4-hydroxyphenyl)propionate | 3.8% |
| methyl 3-(2-tert-butyl-4-hydroxyphenyl)propionate | 85.6% |
| methyl phlorethinate | 2.9% |
| dimeric compound | 6.0% |

After working up by hydrolysis, the monobutylated product has a purity of 92.0% and the melting point is 55°–60° C.

EXAMPLE 2:

396.6 g of 2,6-di-tert-butyl-p-cresol are fused at 150° C. in a nitrogen atmosphere. After addition of 4.97 g of sodium hydrogenphosphate, the reaction mixture is kept for 3½ hours at 150° C. and the pressure in the reactor is adjusted to the range from 20 to 100 mbar. The melt is allowed to cool to room temperature. The analysis of the reaction mixture gives the following values:

| | |
|---|---|
| 2,6-di-tert-butyl-p-cresol | 7.8% |
| 2-tert-butyl-p-cresol | 85.0% |
| p-cresol | 7.0% |

The monobutylated product has a purity of 85% and the melting point is 47°–50° C.

EXAMPLE 3:

The procedure of Example 2 is repeated, using 396.6 g of 4,6-di-tert-butyl-p-cresol and keeping the reaction mixture for 4½ hours at 150° C. after addition of 4.97 g of sodium hydrogensulfate. After cooling to room temperature, the reaction mixture has the following composition:

| 4,6-di-tert-butyl-o-cresol | 2.0% |
|---|---|
| 4-tert-butyl-o-cresol | 97.0% |
| o-cresol | 0.6% |

The monobutylated product, which is liquid at room temperature, has a purity of 97%.

What is claimed is:

1. A process for the preparation of a substituted phenol of formula (1)

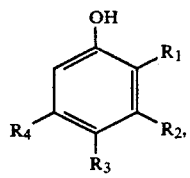

(1)

wherein $R_1$, $R_2$, $R_3$ and $R_4$ are each independently of one another alkyl of 1 to 12 carbon atoms; alkenyl of 2 to 12 carbon atoms; alkynyl of 2 to 12 carbon atoms; or said alkyl, said alkenyl or said alkynyl substituted by hydroxyl, by alkoxy of 1 to 18 carbon atoms, by phenyl or by —COOZ where Z is hydrogen, alkyl of 1 to 18 carbon atoms or —$(C_2H_4O)_n$-H where n is 1 to 12, which process comprises heating a phenol of formula (2)

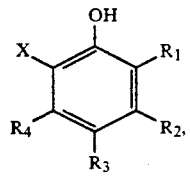

(2)

wherein

X is a secondary or tertiary alkyl of 3 to 12 carbon atoms, and $R_1$, $R_2$, $R_3$ and $R_4$ are as defined above, to a temperature of 120°–170° C., which is above the melting point of the phenol of formula (2), in the presence of an effective catalytic amount of an alkali metal hydrogensulfate catalyst to remove substituent X, and allowing the melt to cool.

2. A process according to claim 1, which comprises heating a phenol of formula

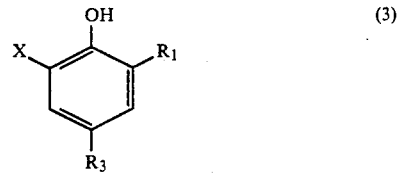

(3)

wherein $R_1$, $R_3$ and X have the given meanings as defined in claim 1.

3. A process according to claim 2, which comprises heating a phenol of formula (3), wherein $R_1$ is hydrogen, alkyl of 1 to 12 carbon atoms, benzyl, phenylethyl or phenylpropyl, $R_3$ is alkyl of 1 to 8 carbon atoms or said alkyl substituted by phenyl or —$CO_2Z$, wherein Z is hydrogen, alkyl of 1 to 18 carbon atoms or —$(C_2H_4O)_n$-H, wherein n is 1 to 12, and X is tertiary alkyl of 4 to 9 carbon atoms.

4. A process according to claim 3, which comprises heating a phenol of formula (3), wherein $R_3$ is methyl, tert-butyl or —$CH_2CH_2CO_2Z$, wherein Z is as defined in claim 3.

5. A process according to claim 1, which comprises heating a phenol of formula

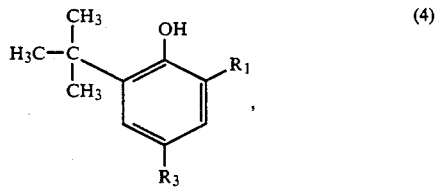

(4)

wherein $R_1$ is hydrogen or alkyl of 1 to 5 carbon atoms, and $R_3$ is alkyl of 1 to 4 carbon atoms or —$CH_2CH_2CO_2CH_3$.

6. A process according to claim 5, which comprises heating a phenol of formula (4), wherein $R_1$ is methyl or tert-butyl and $R_3$ is methyl, tert-butyl or —$CH_2CH_2CO_2CH_3$.

* * * * *